United States Patent
Yoshioka et al.

(10) Patent No.: US 12,344,681 B2
(45) Date of Patent: Jul. 1, 2025

(54) CELLULOSE ACETATE AND METHOD FOR PRODUCING CELLULOSE ACETATE

(71) Applicant: DAICEL CORPORATION, Osaka (JP)

(72) Inventors: Shuuji Yoshioka, Tokyo (JP); Toshikazu Nakamura, Tokyo (JP); Shu Shimamoto, Tokyo (JP); Takao Kishimoto, Imizu (JP)

(73) Assignee: DAICEL CORPORATION, Osaka (JP)

( * ) Notice: Subject to any disclaimer, the term of this patent is extended or adjusted under 35 U.S.C. 154(b) by 802 days.

(21) Appl. No.: 17/612,651

(22) PCT Filed: Jun. 24, 2020

(86) PCT No.: PCT/JP2020/024720
§ 371 (c)(1),
(2) Date: Nov. 19, 2021

(87) PCT Pub. No.: WO2021/002250
PCT Pub. Date: Jan. 7, 2021

(65) Prior Publication Data
US 2022/0227891 A1    Jul. 21, 2022

(30) Foreign Application Priority Data

Jul. 1, 2019    (JP) .................................. 2019-122736

(51) Int. Cl.
| | | |
|---|---|---|
| *A61P 3/04* | (2006.01) | |
| *A61K 31/717* | (2006.01) | |
| *A61P 3/06* | (2006.01) | |
| *C08B 3/06* | (2006.01) | |
| *C08B 3/24* | (2006.01) | |
| *C08B 3/28* | (2006.01) | |

(52) U.S. Cl.
CPC .............. *C08B 3/06* (2013.01); *A61K 31/717* (2013.01); *A61P 3/04* (2018.01); *A61P 3/06* (2018.01); *C08B 3/24* (2013.01); *C08B 3/28* (2013.01)

(58) Field of Classification Search
CPC .... C08B 3/06; C08B 3/24; C08B 3/28; A61K 31/717; A61P 3/04; A61P 3/06
See application file for complete search history.

(56) References Cited

U.S. PATENT DOCUMENTS

| | | |
|---|---|---|
| 2016/0032020 A1 | 2/2016 | Ukita et al. |
| 2016/0317568 A1* | 11/2016 | Shimamoto ............... A61P 1/00 |
| 2017/0100426 A1 | 4/2017 | Shimamoto et al. |

FOREIGN PATENT DOCUMENTS

| | | |
|---|---|---|
| JP | 57-65701 A | 4/1982 |
| JP | H05-500684 A | 2/1993 |
| JP | 6453851 B2 | 1/2019 |
| WO | WO91/16359 A1 | 10/1991 |
| WO | WO2014/142166 A1 | 9/2014 |

OTHER PUBLICATIONS

Genung, L.B., Analytical Chemistry, 1964, 36(9), p. 1817-1821. (Year: 1964).*
Extended European Search Report for European Application No. 20828944.7, dated May 31, 2023.
Author Unknown, "Plastics—Determination of the viscosity of polymers in dilute solution using capillary viscometers—Part 1: General principles," International Standard, ISO-1628-1, 2009, 22 total pages.
Author Unknown, "Plastics—Determination of the viscosity of polymers in dilute solution using capillary viscometers—Part 1: General principles," JIS 7367-1, 2002, 16 total pages.
Buchanan et al., "Preparation and Characterization of Cellulose Monoacetates: The Relationship between Structure and Water Solubility," Macromolecules, vol. 24, 1991, pp. 3060-3064.
Den Besten et al., "The role of short-chain fatty acids in the interplay between diet, gut microbiota, and host energy metabolism," Journal of Lipid Research, vol. 54, 2013, pp. 2325-2340.
English Translation of International Preliminary Report on Patentability for PCT/JP2020/024720 (PCT/IPEA/409) completed on Apr. 23, 2021.
Frost et al., "The short-chain fatty acid acetate reduces appetite via a central homeostatic mechanism," Nature, Apr. 29, 2014, pp. 1-11.
Genda et al., "Bacterial Fermentation of Water-Soluble Cellulose Acetate Raises Large-Bowel Acetate and Propionate and Decreases Plasma Cholesterol Concentrations in Rats," Journal of Agricultural and Food Chemistry, vol. 66, 2018, p. 11909-11916.
Kamide et al., "Dilute Solution Properties of Water-Soluble Incompletely Substituted Cellulose Acetate," Polymer Journal, vol. 13, No. 5, 1981, pp. 421-431.
Miwa et al., "High-Performance Liquid Chromatographic Analysis of Serum Long-Chain Fatty Acids by Direct Derivatization Method," Journal of Chromatography, vol. 416, 1987, pp. 237-245.
Puls et al., "4.3 Degradation and Modification of Cellulose Acetates by Biological Systems," Macromol. Symp., vol. 208, 2004, pp. 239-253.
Reeves et al., "AIN-93 Purified Diets for Laboratory Rodents: Final Report of the American Institute of Nutrition Ad Hoc Writing Committee on the Reformulation of the AIN-76A Rodent Diet," The Journal of Nutrition, vol. 123, 1993, pp. 1939-1951.
Sleeth et al., "Free fatty acid receptor 2 and nutrient sensing: a proposed role for fibre, fermentable carbohydrates and short-chain fatty acids in appetite regulation," Nutrition Research Reviews, vol. 23, 2010, pp. 135-145.

(Continued)

*Primary Examiner* — Jonathan S Lau
(74) *Attorney, Agent, or Firm* — Birch, Stewart, Kolasch & Birch, LLP

(57) ABSTRACT

The present invention is to provide a cellulose acetate that has a low total degree of acetyl substitution and a degree of acetyl substitution at 6-position that is lower compared to the degrees of acetyl substitution at 2-position and 3-position of a glucose ring, and has excellent water solubility. A cellulose acetate having: a total degree of acetyl substitution of 0.4 or greater and 0.9 or less, a proportion of a degree of acetyl substitution at 6-position in the total degree of acetyl substitution of 0% or greater and 18% or less, and a light transmittance at 660 nm of 5% or greater in 4 wt. % aqueous solution.

17 Claims, No Drawings

(56) References Cited

OTHER PUBLICATIONS

Strobel, "Vitamin B12-Dependent Propionate Production by the Ruminal Bacterium Prevotella ruminicola 23," Applied and Environmental Microbiology, vol. 58, No. 7, Jul. 1992, pp. 2331-2333.
Takeda et al., "Synthesis and enzymatic degradation of randomly substituted 2.3.6-0-cellulose acetate and regioselectively substituted 2,3-0-cellulose acetate," Polymer Degradation and Stability, vol. 129, 2016, pp. 125-132.
Tezuka et al., "Determination of substituent distribution in cellulose acetate by means of a 13C NMR study on its propanoated derivative," Carbohydrate Research, vol. 273, 1995, pp. 83-91.

* cited by examiner

CELLULOSE ACETATE AND METHOD FOR PRODUCING CELLULOSE ACETATE

TECHNICAL FIELD

The present invention relates to a cellulose acetate and a method for producing a cellulose acetate.

BACKGROUND ART

It has been known that, when a cellulose acetate with a low degree of substitution having a total degree of acetyl substitution from 0.4 to 1.1 and a water-soluble cellulose acetate having a total degree of acetyl substitution of approximately 0.8 (which is a cellulose acetate with a low degree of substitution) are metabolized and decomposed by intestinal bacteria, physiological actions such as suppression of body weight gain and reduction of blood cholesterol are exhibited (Patent Document 1 and Non-Patent Literature 1).

Major decomposition products of metabolism of the cellulose acetate with a low degree of substitution are acetic acid and propionic acid. Propionic acid is considered to be formed from glucose constituting cellulose via phosphoenolpyruvic acid and succinic acid (Non-Patent Literature 2 and Non-Patent Literature 3). Acetic acid is considered to be formed when acetic acid bonded to cellulose in the cellulose acetate with a low degree of substitution is eliminated, and also from glucose constituting cellulose via phosphoenolpyruvic acid (Non-Patent Literature 2 and Non-Patent Literature 3).

Acetic acid and propionic acid, which are formed when cellulose acetate with a low degree of substitution is metabolized and decomposed by intestinal bacteria, are known to act on, for example, nuclear receptors GPR43 in intestinal L cells and form incretin GLP-land thus affect appetite and saccharometabolism (Non-Patent Literature 4) while the acetic acid and the propionic acid act on hypothalamus and affect appetite suppression, suppression of body weight gain, saccharometabolism, and lipid metabolism (Non-Patent Literature 5).

For deacetylation of the cellulose acetate with a low degree of substitution, acetylxylan esterase which is an enzyme is known to be related (Non-Patent Literature 6). Note that, *Bacteroides xylanisolvens* (Patent Document 1, Non-Patent Literature 1) that proliferates in an intestine of a rat to which cellulose acetate with a low degree of substitution is given has been well-researched as xylan decomposition bacteria and is thought to have acetylxylan esterase. Based on these, it is presumed that the first decomposition in the metabolic decomposition of the cellulose acetate with a low degree of substitution by intestinal bacteria is deacetylation, and acetylxylan esterase is considered to be related to this decomposition.

Hydroxy groups are present at 2-position, 3-position, and 6-position of glucose contained as a main constituent of cellulose. In a cellulose acetate with a low degree of substitution, some of these hydroxy groups are acetylated. Acetylxylan esterase selectively eliminates an acetyl group present at the 2-position or the 3-position but hardly eliminates an acetyl group at the 6-position (Non-Patent Literature 6).

CITATION LIST

Patent Documents

Patent Document 1: JP 6453851 B

Non-Patent Literature

Non-Patent Literature 1: Genda et al., Journal of Agricultural and Food Chemistry, 66, 11909-11916 (2018).
Non-Patent Literature 2: Gijs den Besten et al., Journal of Lipid Research, 54, 2325-2340 (2013).
Non-Patent Literature 3: Strobel, Applied and Environmental Microbiology, 58, 2331-2333 (1992).
Non-Patent Literature 4: Sleeth et al., Nutrition Research Reviews, 23, 135-145 (2010).
Non-Patent Literature 5: Frost et al., Nature Communications, DOI:10.1038 (2014).
Non-Patent Literature 6: Puls et al., Mactomolecular Symposia, 208, 239-253 (2004).
Non-Patent Literature 7: Buchanan et al., Macromolecules, 24, 3060-3064 (1991).

SUMMARY OF INVENTION

Technical Problem

A cellulose acetate with a low degree of substitution is considered to exhibit physiological actions via metabolic decomposition by intestinal bacteria. A cellulose acetate with a low degree of substitution that has biodegradability and a tendency to be metabolized and decomposed by intestinal bacteria is expected to exhibit excellent physiological actions.

Since acetylxylan esterase hardly eliminates an acetyl group at 6-position, to enhance biodegradability of the cellulose acetate with a low degree of substitution, a degree of acetyl substitution at the 6-position needs to be relatively reduced compared to degrees of acetyl substitution of the 2-position and 3-position of a glucose ring of a cellulose acetate.

However, by the known methods, the degree of acetyl substitution at the 6-position could not be relatively reduced compared to the degrees of acetyl substitution of the 2-position and 3-position of the glucose ring in a cellulose acetate having a low total degree of acetyl substitution.

Furthermore, a cellulose acetate having a low degree of substitution and better water solubility enhances biodegradability more. Therefore, a cellulose acetate with a low degree of substitution that has a low degree of acetyl substitution at the 6-position and that has excellent water solubility exhibits especially excellent biodegradability.

However, such a cellulose acetate with a low degree of substitution having a low degree of acetyl substitution at the 6-position with excellent water solubility was not known. For example, the degree of acetyl substitution at 6-position of cellulose acetate with a low degree of substitution described in Patent Document 1 is not low. Non-Patent Literature 7 describes cellulose acetate with a low degree of substitution having a low degree of acetyl substitution at the 6-position as Experiment No. 6 and Experiment No. 7; however, water solubility is poor.

An object of the present invention is to provide a cellulose acetate that has a low total degree of acetyl substitution and a degree of acetyl substitution at 6-position that is lower compared to the degrees of acetyl substitution at 2-position and 3-position of a glucose ring, and has excellent water solubility.

Solution to Problem

The first of the present disclosure relates to a cellulose acetate having: a total degree of acetyl substitution of 0.4 or greater and 0.9 or less, a proportion of a degree of acetyl substitution at 6-position in the total degree of acetyl substitution of 0% or greater and 18% or less, and a light transmittance at 660 nm of 5% or greater in 4 wt. % aqueous solution.

In the cellulose acetate, the light transmittance at 660 nm may be 80% or greater in 4 wt. % aqueous solution.

The second of the present disclosure relates a method for producing the cellulose acetate described above, the method including deacetylating by subjecting a raw material cellulose acetate having a total degree of acetyl substitution from 1.5 to 3.0 to solvolysis, and precipitating a cellulose acetate that is formed by the deacetylating of the raw material cellulose acetate, where the solvolysis of the raw material cellulose acetate is allowed to progress in the presence of a solvent containing an alcohol having 3 carbons or less, and an acid catalyst at a temperature that is not lower than a boiling point of the alcohol.

In the method for producing the cellulose acetate, the acid catalyst may have an acid dissociation constant pKa in water at 25° C. of 0 or less.

In the method for producing the cellulose acetate, the acid catalyst may be sulfuric acid.

In the method for producing the cellulose acetate, the alcohol may be methanol.

In the method for producing the cellulose acetate, the solvent may contain acetate.

In the method for producing the cellulose acetate, the method may include removing a residue by dissolving the precipitated cellulose acetate in water, and depositing the dissolved cellulose acetate.

In the method for producing the cellulose acetate, the method may include removing a residue by dissolving the precipitated cellulose acetate in water and performing centrifugal separation, and reprecipitating the dissolved cellulose acetate.

Advantageous Effects of Invention

According to the present invention, cellulose acetate that has a low total degree of acetyl substitution and a degree of acetyl substitution at 6-position that is lower compared to the degrees of acetyl substitution at 2-position and 3-position of a glucose ring, and that has excellent water solubility can be provided.

DESCRIPTION OF EMBODIMENTS

Cellulose Acetate

The cellulose acetate of the present disclosure has a total degree of acetyl substitution of 0.4 or greater and 0.9 or less, a proportion of a degree of acetyl substitution at 6-position in the total degree of acetyl substitution of 0% or greater and 18% or less, and a light transmittance at 660 nm of 5% or greater in 4 wt. % aqueous solution.

Total Degree of Acetyl Substitution

The cellulose acetate of the present disclosure has a total degree of acetyl substitution of 0.4 or greater and 0.9 or less. When the total degree of acetyl substitution is in this range, the cellulose acetate of the present disclosure has excellent water solubility and biodegradability. Note that the cellulose acetate according to the present disclosure has a total degree of acetyl substitution of 0.4 or greater and 0.9 or less, and this may be referred to as cellulose acetate with a low degree of substitution.

Proportion of Degree of Acetyl Substitution at 6-Position

The cellulose acetate according to the present disclosure, the proportion of a degree of acetyl substitution at 6-position in the total degree of acetyl substitution is 0% or greater and 18% or less, and the proportion of the degree of acetyl substitution at the 6-position is preferably 17% or less, more preferably 14% or less, and even more preferably 10% or less. The proportion of the degree of acetyl substitution at the 6-position is most preferably 0% but may be greater than 0%, 4% or greater, 7% or greater, and 9% or greater. By setting the proportion to 18% or less, excellent degradability by an enzyme (e.g., acetylxylan esterase) present in an intestine is achieved, and metabolism in the body readily occurs.

The total degree of acetyl substitution and the proportion of the degree of acetyl substitution at the 6-position in the total degree of acetyl substitution can be determined by the following method.

First, each degree of acetyl substitution at the 2-position, the 3-position, and the 6-position of a glucose ring in cellulose acetate is measured by the NMR method in accordance with the method by Tezuka (Tezuka, Carbonydr. Res. 273, 83 (1995)). That is, the free hydroxyl group of the cellulose acetate is propionylated with propionic anhydride in pyridine. The resulting sample is dissolved in deuterated chloroform, and the $^{13}$C-NMR spectrum is measured. The carbon signals of the acetyl group appear in the region from 169 ppm to 171 ppm in the order of position 2-, 3-, and 6- from the high magnetic field; and the carbonyl carbon signals of the propionyl group appear in the region from 172 ppm to 174 ppm in the same order. Each degree of acetyl substitution at the 2-position, the 3-position, and the 6-position of the glucose ring in the cellulose acetate can be determined based on the presence ratio of the acetyl group and the propionyl group at the respective corresponding positions. Furthermore, the degree of acetyl substitution can be analyzed by $^1$H-NMR in addition to $^{13}$C-NMR.

The degree of acetyl substitution of position i is a value obtained by dividing the number of moles of acetyl groups of position i by the sum of the number of moles of the acetyl groups and the number of moles of hydroxy groups of position i, and is a real number of 0 to 1. Note that i is any one of 2, 3, or 6. Furthermore, the sum of the degrees of acetyl substitution of positions 2, 3, and 6 of the glucose ring of the cellulose acetate is the total degree of acetyl substitution. Thus, the proportion of the degree of acetyl substitution at the 6-position in the sum of the degrees of acetyl substitution of the 2-, 3-, and 6-positions of the glucose ring of the cellulose acetate is a proportion (%) of the degree of acetyl substitution at the 6-position in the total degree of acetyl substitution.

Note that the total degree of acetyl substitution can be converted into the acetyl value by using the following equation.

$$DS=162.14 \times AV \times 0.01/(60.052-42.037 \times AV \times 0.01)$$

DS: Total degree of acetyl substitution
AV: Acetyl value (%)

Light Transmittance

For the cellulose acetate according to the present disclosure, the light transmittance at 660 nm of 4 wt. % aqueous solution of the cellulose acetate is 5% or greater, and the light transmittance is preferably 10% or greater, more preferably 30% or greater, even more preferably 50% or greater, and most preferably 80% or greater. The light transmittance may be 99% or less, 98% or less, or 95% or less. When the light transmittance at 660 nm of 4 wt. % aqueous solution is less than 5%, water solubility of the cellulose acetate is poor.

The light transmittance at 660 nm of 4 wt. % aqueous solution of the cellulose acetate can be determined by using a spectrophotometer (UV-Vis spectrophotometer UV-1800, available from Shimadzu Corporation; cell material: polystyrene; cell length: 10 mm).

Degree of Polymerization (Viscosity-Average Degree of Polymerization)

The viscosity-average degree of polymerization of the cellulose acetate according to the present disclosure is not particularly limited, and is preferably 3 or greater and 400 or less, more preferably 10 or greater and 200 or less, and even more preferably 15 or greater and 150 or less. By setting the viscosity-average degree of polymerization to the range, especially excellent water solubility and biodegradability are achieved.

The viscosity-average degree of polymerization (DP) can be evaluated as a viscosity-average degree of polymerization based on the limiting viscosity number ([η]; unit: g/mL) as described below. Specifically, the limiting viscosity number is determined by a method in accordance with JIS-K-7367-1 and ISO 1628-1, the viscosity-average molecular weight is calculated in accordance with the literature by Kamide et al., and the viscosity-average degree of polymerization can be calculated based on the viscosity-average molecular weight.

The cellulose acetate according to the present disclosure can be produced by the following production method.

Because the cellulose acetate according to the present disclosure has a low total degree of acetyl substitution and a degree of acetyl substitution at 6-position that is lower compared to the degrees of acetyl substitution at 2-position and 3-position of a glucose ring, the cellulose acetate has excellent degradability by an enzyme (e.g., acetylxylan esterase) present in an intestine, is readily metabolized in the body, and can be utilized as food.

Method for Producing Cellulose Acetate

The method for producing the cellulose acetate according to the present disclosure includes deacetylating by subjecting a raw material cellulose acetate having a total degree of acetyl substitution from 1.5 to 3.0 to solvolysis, and precipitating cellulose acetate that is formed by the deacetylating of the raw material cellulose acetate, where the solvolysis of the raw material cellulose acetate is allowed to progress in the presence of a solvent containing an alcohol having 3 carbons or less and an acid catalyst at a temperature that is not lower than a boiling point of the alcohol.

Deacetylating

In the deacetylating in the method for producing the cellulose acetate according to the present disclosure, the raw material cellulose acetate is subjected to solvolysis. In the deacetylating according to the present disclosure, deacetylation proceeds by the solvolysis. The solvolysis include a case where only a solvent containing an alcohol having 3 carbons or less participates and a case where a solvent containing an alcohol having 3 carbons or less and another solvent such as water participate. The solvolysis also includes hydrolysis.

Raw Material Cellulose Acetate

As the raw material cellulose acetate, cellulose acetate having a middle to high degree of substitution can be used. The total degree of acetyl substitution of the cellulose acetate having a middle to high degree of substitution used as the raw material is from 1.5 to 3.0, and preferably from 1.5 to 2.5. As the raw material cellulose acetate, commercially available cellulose diacetate (total degree of acetyl substitution: 2.20 to 2.56) or cellulose triacetate (total degree of acetyl substitution: greater than 2.56 and 3 or less) can be used.

When the raw material cellulose acetate is produced, the production may be performed by a known production method. For example, production can be performed by a series of process including disintegrating pulp which is a cellulose raw material, pretreating, acetylating, hydrolyzing, precipitating, and adding a stabilizer. Each of these processes will be described. Note that typical cellulose acetate production method can be found in "Wood Chemistry (Volume I)" (Migita et al., published by Kyoritsu Shuppan Co., Ltd. in 1968, pp. 180-190).

The α-cellulose content of the pulp is preferably 92 wt. % or greater, more preferably 93 wt. % or greater, and even more preferably 94 wt. % or greater. The upper limit is not particularly limited, but the upper limit may be 99 wt. % or less. Such high purity pulp contains almost no lignin derived from wood and also contains only a little hemicellulose. This is because cellulose acetate having especially excellent water solubility and biodegradability can be obtained due to these impurities being contained in only a little amount.

The α-cellulose content can be determined in the following manner. Pulp having a known weight is continuously subjected to extraction at 25° C. using a 17.5% aqueous sodium hydroxide solution and a 9.45% aqueous sodium hydroxide solution, and then a soluble fraction in the extraction solution is oxidized with potassium dichromate. The weight of β,γ-cellulose is determined from the volume of potassium dichromate used for oxidization. A value obtained by subtracting the weight of β,γ-cellulose from the initial weight of the pulp is defined as the weight of insoluble fraction of the pulp, the weight of α-cellulose (TAPPI T203). The ratio of the weight of insoluble fraction of the pulp to the initial weight of the pulp is defined as the α-cellulose content (wt. %).

As pulp, wood pulp (softwood pulp, hardwood pulp), and cotton linters can be used. These celluloses may be used alone or in combination of two or more; for example, softwood pulp and cotton linters or hardwood pulp may be used in combination.

Wood pulp is preferred because of stable supply of the raw material and advantages in cost effectiveness compared to linters. Examples of the wood pulp include hardwood prehydrolysis kraft pulp.

In the disintegrating of pulp, for example, dry disintegration can be performed by using a disc refiner.

In the pretreating, the disintegrated pulp is brought into contact with acetic acid or acetic acid-with-sulfuric acid. As the acetic acid, from 96 to 100 wt. % acetic acid can be used. The acetic acid-with-sulfuric acid is acetic acid containing sulfuric acid, and from 1 to 10 wt. % of sulfuric acid is preferably contained.

In the acetylating, the pretreated pulp is brought into contact with a mixed solution of acetic acid and acetic anhydride to acetylate the pulp with the acetic anhydride, and thus a fully trisubstituted cellulose acetate (primary cellulose acetate) is obtained. In the mixed solution, sulfuric acid is preferably contained as a catalyst. In the acetylating, from 96 to 100 wt. % acetic acid can be used as the acetic acid, the sulfuric acid is preferably concentrated sulfuric acid.

In the hydrolyzing, a neutralizing agent such as water, diluted acetic acid, or an aqueous solution of magnesium acetate is added to neutralize (complete neutralization or partial neutralization) the sulfuric acid and deactivate the acetic anhydride, and the acetylation reaction is terminated. As a result, the fully trisubstituted cellulose acetate (primary cellulose acetate) is hydrolyzed, and cellulose acetate having a desired degree of substitution (secondary cellulose acetate)

is obtained. Note that the diluted acetic acid refers to a 1 to 50 wt. % aqueous solution of acetic acid. Furthermore, the magnesium acetate concentration of the aqueous solution of magnesium acetate is preferably from 5 to 30 wt. %.

In the precipitating, a mixture containing the cellulose acetate and a precipitating agent such as water, diluted acetic acid, a diluted aqueous solution of calcium hydroxide, or an aqueous solution of magnesium acetate are mixed, and the cellulose acetate is precipitated. Furthermore, the formed cellulose acetate (precipitate) is separated and water-washed to remove free metal components and sulfuric acid components.

In the adding a stabilizer, in addition to washing with water, an alkali metal compound and/or an alkaline earth metal compound, and in particular a calcium compound, such as calcium hydroxide, may be added as a stabilizer as necessary. Furthermore, a stabilizer may be used during washing with water.

Solvolysis of Raw Material Cellulose Acetate The solvolysis of the raw material cellulose acetate progresses in the presence of a solvent containing an alcohol having 3 carbons or less and an acid catalyst at a temperature that is not lower than a boiling point of the alcohol.

The solvent containing an alcohol having 3 carbons or less is only required to be a solvent that contains an alcohol having 3 carbons or less and that can dissolve the raw material cellulose acetate. "Can dissolve the raw material cellulose acetate" means the state in which some or all of the raw material cellulose acetate can be subjected to molecular dispersion under condition of being heated or not heated and means that clear change of the form or disappearance of the solid raw material cellulose acetate can be visually observed.

The alcohol having 3 carbons or less contained in the solvent is not particularly limited. Examples thereof include methanol, ethanol, 1-propanol, and 2-propanol. Among these, methanol and ethanol are preferred, and methanol is more preferred.

In the solvent, the content of the alcohol having 3 carbons or less is preferably 70 wt. % or greater, and more preferably 80 wt. % or greater. Furthermore, the content may be 100 wt. % or less.

The solvent may contain an optional component such as acetate, acetic acid, and acetone, in addition to the alcohol having 3 carbons or less. Among these, acetate is preferred. Among the acetates, ethyl acetate and methyl acetate are more preferred. This is because solubility of the starting material (raw material cellulose acetate) and/or reaction intermediate material to the reaction bath is enhanced and cellulose acetate having excellent water solubility and biodegradability can be obtained.

In the solvent, the content of the optional component other than the alcohol having 3 carbons or less is preferably 30 wt. % or less, and more preferably 20 wt. % or less. In particular, when acetate is contained as the optional component, the content of the acetate in the solvent is preferably 5 wt. % or greater and 10 wt. % or less.

The used amount of the solvent containing an alcohol having 3 carbons or less is, for example, from 0.5 to 50 parts by weight, preferably from 1 to 20 parts by weight, and more preferably from 3 to 10 parts by weight, relative to 1 part by weight of the raw material cellulose acetate.

An acid catalyst commonly used as a deacetylation catalyst can be used as the catalyst. Examples of the acid catalyst include inorganic acids such as sulfuric acid, hydrochloric acid, and phosphoric acid; and organic acids such as trifluoroacetic acid and formic acid. One type of these acid catalysts or a combination of two or more types of these acid catalysts may be used.

The acid catalyst preferably has an acid dissociation constant pKa in water at 25° C. of 0 or less, more preferably −0.5 or less, and even more preferably −1.0 or less. The acid dissociation constant pKa may be −6.0 or greater.

The acid catalyst is preferably sulfuric acid. Furthermore, for the sulfuric acid, an aqueous solution of sulfuric acid having a sulfuric acid concentration of 98 wt. % can be used as a concentrated sulfuric acid. The catalyst may be mixed with the solvent containing an alcohol having 3 carbons or less in advance and used in the solvolysis of the raw material cellulose acetate.

The used amount of the acid catalyst is, for example, preferably from 0.005 to 1 part by weight, more preferably from 0.01 to 0.5 parts by weight, and even more preferably from 0.02 to 0.3 parts by weight, relative to 1 part by weight of the raw material cellulose acetate. When the amount of the catalyst is too small, the time of the solvolysis becomes excessively long, and this is not economically preferred although there is an advantage in that control of the reaction end is made easy. On the other hand, when the amount of the catalyst is too large, the degree of change in depolymerization rate with respect to the solvolysis temperature becomes greater, the control of the reaction end becomes difficult, and the cellulose acetate having the total degree of substitution according to the present disclosure is less likely to be obtained. Furthermore, nonuniform cellulose acetate having uneven degree of acetyl substitution tends to be formed.

The content of water in the solvolysis reaction system is preferably smaller, and preferably 2 parts by weight or less, more preferably 1 part by weight or less, and even more preferably 0.5 parts by weight or less, relative to 1 part by weight of the raw material cellulose acetate. Furthermore, it is only required to start and proceed the solvolysis of the raw material cellulose acetate, and the lower limit of the content of water in the solvolysis reaction system is not limited and, for example, may be 0.01 parts by weight or greater relative to 1 part by weight of the raw material cellulose acetate.

When the raw material cellulose acetate is subjected to solvolysis, water originally contained in the raw material cellulose acetate may be removed in advance or not removed. The water content percentage of the raw material cellulose acetate may be, for example, 5 wt. % or less, 4 wt. % or less or 3 wt. % or less, and 1 wt. % or greater, in the raw material cellulose acetate.

The water content percentage of the raw material cellulose acetate can be measured by the following method. The measurement can be performed by using a Kett moisture meter (METTLER TOLEDO HB43). Approximately 2.0 g of a sample in a water-containing state is placed on an aluminum sample pan of the Kett moisture meter and heated at 120° C. until the weight does not change, and the water content percentage (wt. %) in the sample can be calculated from the weight change before and after the heating.

In the deacetylating of the raw material cellulose acetate by solvolysis, in addition to the water originally contained in the raw material cellulose acetate, water may be added to the system. The entire amount of water may be present in the system at the start of the reaction, and a part of the water used may be present in the system at the start of the reaction and the rest of the water may be added into the system in one to several portions.

The content of water in the solvolysis reaction system is preferably 20 parts by weight or less, more preferably 10 parts by weight or less, and even more preferably 5 parts by weight or less, relative to 1 part by weight of the solvent.

The temperature of the solvolysis reaction system is adjusted to a temperature that is not lower than the boiling point of the alcohol having 3 carbons or less. For example, in a case where methanol is used as the alcohol having 3 carbons or less, the temperature is 65° C. or higher; in a case where ethanol is used, the temperature is 78° C. or higher; in a case where 1-propanol is used, the temperature is 97° C. or higher; and in a case where 2-propanol is used, the temperature is 82° C. or higher. The raw material cellulose acetate can be sufficiently dissolved in the solvent, and the solvolysis reaction can be uniformly progressed.

The temperature of the solvolysis reaction system is not limited as long as the temperature is not lower than the boiling point of the alcohol having 3 carbons or less and is preferably 105° C. or lower, more preferably 100° C. or lower, and even more preferably 95° C. or lower. When the temperature is higher than 105° C., decrease in the degree of polymerization of the obtained cellulose acetate and decrease in the yield become significant.

The gauge pressure in the solvolysis reaction system is preferably 0.2 MPaG or greater and 1 MPaG or less. The gauge pressure is preferably 0.2 MPaG or greater and 0.7 MPaG or less, and more preferably 0.2 MPaG or grater and 0.5 MPaG or less. By setting the gauge pressure to 0.2 MPaG or greater, the raw material cellulose acetate can be sufficiently dissolved in the solvent, and the solvolysis reaction can be especially uniformly progressed. When the gauge pressure is greater than 1 MPaG, decrease in the degree of polymerization of the obtained cellulose acetate and decrease in the yield become significant.

The time of the solvolysis reaction may be 20 minutes or longer and 300 minutes or less, 30 minutes or longer and 240 minutes or less, 60 minutes or longer and 200 minutes or less, and 60 minutes or longer and 150 minutes or less. By setting the time to this range, adjustment to the total degree of acetyl substitution of 0.4 or greater and 0.9 or less becomes easy.

Note that the time of the solvolysis reaction refers to a time for maintaining a temperature from the time at which the temperature of the solvolysis reaction system is reached.

In deacetylation of a raw material cellulose acetate in the related art, the raw material cellulose acetate is dissolved in acetic acid and water-mixed solvent, and the raw material cellulose acetate is hydrolyzed by using a sulfuric acid catalyst. At this time, elimination of acetyl groups progresses in almost the same manner as for 2-position, 3-position, and 6-position of a glucose ring of the cellulose acetate. On the other hand. in the method for producing the cellulose acetate according to the present disclosure, the acetyl group at 6-position is preferentially eliminated, and cellulose acetate having a low degree of acetyl substitution at 6-position compared to degrees of acetyl substitution at 2-position and 3-position of the glucose ring can be obtained.

In deacetylation of a raw material cellulose acetate in the related art, acetic acid is used as the reaction solvent, and the reaction progresses while acetic acid preferentially re-acetylating 6-position during the deacetylation, apparently, elimination of acetyl groups progresses almost in the same manner for 2-position, 3-position, and 6-position of the glucose ring of the cellulose acetate. If re-acetylation of 6-position is suppressed, cellulose acetate having a low degree of substitution of 6-position can be obtained; however, in this case, a solvent in place of the acetic acid is required. As a result of diligent research, the inventors of the present invention found that solvents containing alcohols having 3 carbons or less are suitable for reaction solvents for this purpose at a temperature of not lower than the boiling point. A solvent containing an alcohol having 3 carbons or less dissolves or highly swells cellulose acetate having a middle to high degree of substitution of a starting material at a temperature of not lower than the boiling point.

The solvolysis of the raw material cellulose acetate can be terminated by addition of a neutralizing agent. Examples of the neutralizing agent include weak acid salts, such as acetate salts, such as sodium acetate and magnesium acetate, and carbonates, such as sodium carbonate and magnesium carbonate. The neutralizing agent may be added together with the solvent containing an alcohol having 3 carbons or less.

The used amount of the neutralizing agent is preferably from 1.0 to 5.0 equivalents, preferably from 1.1 to 3.0 equivalents, and more preferably from 1.2 to 2.0 equivalents, relative to 1 equivalent of the acid catalyst. In a case where the amount of the neutralizing agent is too small, the acid catalyst may remain in the cellulose acetate with a low degree of substitution, and decomposition of cellulose acetate with a low degree of substitution may occur. On the other hand, when the amount of the neutralizing agent is too large, a large amount of solvents are used for washing the neutralizing agent, which is not economically preferred.

Precipitating

In the precipitating in the method for producing the cellulose acetate according to the present disclosure, cellulose acetate formed by the deacetylation of the raw material cellulose acetate is precipitated.

Examples of the method of precipitation include a method in which, after completion of the solvolysis reaction of the raw material cellulose acetate, cellulose acetate having a low degree of substitution is precipitated by reducing the temperature of the reaction system to room temperature. Thus, in the method of precipitation by cooling, addition of precipitating solvent is not required, and the method is economically preferred. By adding a precipitating solvent, precipitation of the cellulose acetate having a low degree of substitution may be promoted, and the yield may be increased, and thus a precipitating solvent may be added.

Examples of the precipitating solvent include the solvent containing an alcohol having 3 carbons or less described above; ketones such as acetone and methyl ethyl ketone; esters such as ethyl acetate and methyl acetate; nitrogen-containing compounds such as acetonitrile; ethers such as tetrahydrofuran; and mixed solvents of these. One type of these precipitating solvents may be used, or a mixed solvent containing two or more types of the solvents may be used. Among these, when the solvent that is the same as the reaction solvent is used as the precipitating solvent, recovery and reuse of the solvent waste may become easier, and thus the solvent containing an alcohol having 3 carbons or less is preferred.

The precipitating solvent preferably contains a basic substance described below. This is because the neutralization and the precipitation can be performed simultaneously.

Optional Process

Washing and Neutralizing

The precipitate cellulose acetate is preferably washed with an organic solvent (poor solvent), such as an alcohol such as methanol and a ketone such as acetone. It is also preferable to perform washing and neutralization with an organic solvent (e.g., an alcohol such as methanol or a ketone such as acetone) containing a weak acid salt and/or a basic substance. The washing and neutralization can efficiently remove impurities including the catalyst (such as sulfuric acid) used in the solvolysis.

Examples of the weak acid salts include hydrates of acetate salts, such as sodium acetate and magnesium acetate, and hydrates of carbonates, such as sodium carbonate and magnesium carbonate. Examples of the basic substance include alkali metal compounds such as alkali metal hydroxides such as calcium hydroxide.

Purification

By further subjecting the precipitated cellulose acetate to purification, cellulose acetate having excellent water solubility can be obtained. In particular, when the total degree of acetyl substitution of the raw material cellulose acetate is higher, the water solubility of the resulting cellulose acetate tends to be reduced, purification is preferably performed. Purification can be performed by, for example, precipitation fractionation (fractional precipitation) and/or dissolution fractionation (fractional dissolution).

Dissolution fractionation can be performed by, for example, forming a water-based solution by dissolving the precipitated cellulose acetate (solid) in water or a mixed solvent of water and a hydrophilic organic solvent (e.g., acetone) and removing residues (i.e., insoluble components). As the method of removing the residues, centrifugal separation may be employed.

The dissolution of the cellulose acetate is only required to be performed by agitating at an appropriate temperature (e.g., from 20 to 80° C., and preferably from 25 to 60° C.). Furthermore, the concentration of the cellulose acetate in the water-based solution (blending proportion) is only required to be adjusted to an appropriate concentration (e.g., from 2 to 10 wt. %, and preferably from 3 to 8 wt. %).

Furthermore, in a case where the mixed solvent of water and a hydrophilic organic solvent is used, the concentration of the organic solvent in the mixed solvent is, for example, from 5 to 50 wt. %, and preferably from 10 to 40 wt. %.

After the residues are removed, the dissolved cellulose acetate is only required to be deposited. Examples of the method of deposition include reprecipitation and spray drying. Examples of the precipitating solvent used for the reprecipitation include the solvent containing an alcohol having 3 carbons or less described above; ketones such as acetone and methyl ethyl ketone; esters such as ethyl acetate and methyl acetate; nitrogen-containing compounds such as acetonitrile; ethers such as tetrahydrofuran; and mixed solvents of these. One type of these precipitating solvents may be used, or a mixed solvent containing two or more types of the solvents may be used.

Stabilizer Addition

After the cellulose acetate is precipitated, a stabilizer may be added to the precipitated cellulose acetate. This is to enhance thermal stability of the cellulose acetate. As the stabilizer, an alkali metal compound and/or an alkaline earth metal compound, and in particular a calcium compound such as calcium hydroxide, are preferred.

For the addition amount of the stabilizer, for example, addition is preferably performed in a volume ratio of a reaction mixture containing cellulose acetate to an aqueous solution of calcium hydroxide adjusted to from 0.2 to 1.0 wt. % of 100:1 to 10.

The addition of the stabilizer may be performed at the same time of removal of free metal components and/or sulfuric acid components by washing using a poor solvent such as a precipitating solvent of the precipitate.

After precipitating the deacetylated cellulose acetate or after an optional process in a case where such optional process is included, the cellulose acetate is preferably dried.

In a case where the cellulose acetate is dried, the method of drying is not particularly limited, and a known method can be used. Examples thereof include drying such as air drying such as hot-air drying, drying under reduced pressure, and vacuum drying. The temperature and the pressure are only required to be appropriately adjusted.

After the cellulose acetate is dried, the cellulose acetate may be pulverized. The pulverization can be performed by using a known pulverizer, such as a sample mill, hammer mill, turbo mill, atomizer, cutter mill, bead mill, ball mill, roll mill, jet mill, and pin mill. Furthermore, freezing and crushing, dry crushing at room temperature, or wet crushing may be performed.

EXAMPLES

Hereinafter, the present invention will be specifically described with reference to examples, but the technical scope of the present invention is not limited by these examples.

Preparation and Physical Properties of Cellulose Acetate

For the cellulose acetates of Examples and Comparative Examples, measurements of physical properties listed in Table 1 were performed as describe below.

Reaction Product Yield

The reaction product yield (yield of cellulose acetate before the purification) (wt. %) was calculated as described below.

Reaction product yield (wt. %)=actual yield of solvolysis reaction product (cellulose acetate before purification in a case purification is included)/ideal yield of solvolysis reaction product (cellulose acetate before purification in a case purification is included)

Purified Product Yield

The purified product yield (wt. %) was calculated as below.

Purified product yield (yield of cellulose acetate after purification) (wt. %)=actual yield of purified product (cellulose acetate after purification in a case purification is included)/actual yield of solvolysis reaction product (cellulose acetate before purification in a case purification is included)

Total Degree of Acetyl Substitution, Degree of Acetyl Substitution of Each of 2-Position, 3-Position, and 6-Position ($DS_2$, $DS_3$, and $DS_6$), Proportion of Degree of Acetyl Substitution at 6-Position in Total Degree of Acetyl Substitution In accordance with the literature by Tezuka et al. (Carbohydrate Research, 273, 83-91 (1995)), after the sample was propionylated with propionic anhydride in a pyridine solvent, the sample was subjected to $^{13}C$-NMR spectroscopy using a chloroform solvent. The intensities of 3 signals of acetyl carbonyl carbons appeared around 169.1 to 170.2 ppm were integrated, and the intensities of 3 signals of propionyl carbonyl carbons appeared around 172.7 to 173.6 ppm were integrated.

In $^{13}C$-NMR spectrum, the 3 signals of acetyl carbonyl carbon appeared around 169.1 to 170.2 ppm are each assigned to 2-, 3-, and 6-positions from the side of upfield. The intensity in the range of ±0.2 ppm for maximum of each of the signals was integrated, and this was defined as the integrated intensity of each acetyl carbonyl carbon signal, and $DS_i$ (i is 2, 3, or 6) was determined based on the following equation.

$$DS_i = DS \times (\text{acetyl carbonyl carbon signal integrated intensity for position } i)/(\text{sum of acetyl carbonyl carbon signal integrated intensities for positions 2, 3, and 6})$$

NMR measurement conditions are as follows.
Measurement solvent: $CDCl_3$ (approximately 3 mL was used)
Measurement temperature: 40° C.
Sample amount: 160 to 180 mg ($\varphi$ 10 mm)
Observed nucleus: 13C (1H complete decoupling)
Number of data point: 32768
Pulse angle and time: 45°, 9 μsec
Data acquisition time: 0.9667 sec
Latency: 2.0333 sec
Number of accumulation: 18000 scans The total degree of acetyl substitution (DS) was determined by the following equation taking acetyl carbonyl carbon signal integrated intensity as X and propionyl carbonyl carbon signal integrated intensity as Y.

$$\text{Total degree of acetyl substitution (DS)} = 3 \times [X/(X+Y)]$$

The proportion (%) of the degree of acetyl substitution at the 6-position in the total degree of acetyl substitution was determined by the following equation. Proportion of degree of acetyl substitution at 6-position (%)=degree of acetyl substitution at 6-position ($DS_6$)/total degree of acetyl substitution (DS)×100

Degree of Polymerization (Viscosity-Average Degree of Polymerization)

The degree of polymerization of the cellulose acetate was evaluated as the viscosity-average degree of polymerization based on the limiting viscosity number ([η], unit: g/mL).

Specifically, first, in accordance with JIS-K-7367-1 and ISO1628-1, by using a Ubbelohde viscometer with the size number 1C as a viscometer and by using dimethyl sulfoxide (DMSO) as a solvent, the limiting viscosity number of the cellulose acetate was determined based on a value obtained by dividing the logarithmic relative viscosity at 25° C. by the concentration.

Next, the molecular weight (viscosity-average molecular weight) of cellulose acetate was determined by the following equation in accordance with the literature by Kamide et al.

$$\text{Viscosity-average molecular weight} = (\text{limiting viscosity number}[\eta]/0.171)^{(1/0.61)}$$

Then, the degree of polymerization of the cellulose acetate (viscosity-average degree of polymerization) was determined by the following equation.

$$\text{Degree of polymerization(viscosity-average degree of polymerization)} = \text{viscosity-average molecular weight}/(162.14+42.037 \times DS)$$

Transmittance (Light Transmittance of 4 wt. % Aqueous Solution)

In 10 mL of water, 0.4 g of cellulose acetate was dispersed, agitated by a magnetic stirrer for 2 hours, allowed to stand still overnight, and agitated again for 2 hours. The light transmittance (%) of 660 nm of 4% aqueous solution of the cellulose acetate that was obtained as described above was measured by using a spectrophotometer (UV-Vis spectrophotometer UV-1800, available from Shimadzu Corporation; cell material: polystyrene; cell length: 10 mm).

Example A-1

Deacetylating:

In 554 parts by weight of methanol as a solvent, 70 parts by weight of cellulose diacetate (trade name "L-50", available from Daicel Corporation; water content percentage: 3 wt. %; total degree of acetyl substitution: 2.43; degree of acetyl substitution at 2-position: 0.86; degree of acetyl substitution at 3-position: 0.82; degree of acetyl substitution at 6-position: 0.75) as a raw material cellulose acetate was added at room temperature, and 3.5 parts by weight of sulfuric acid was further added as a catalyst. While this mixture was agitated, the temperature of the mixture was increased to 90° C. over the temperature increase time of 50 minutes, and then the temperature was adjusted (maintained) at 90° C. for 100 minutes.

Precipitating:

The reaction mixture was cooled to room temperature, then a mixture of 14.6 parts by weight of sodium acetate trihydrate and 55 parts by weight of methanol was added, and thus the sulfuric acid was neutralized. The white solid suspended in the reaction mixture was filtered by vacuum filtration. The filtered white solid was suspended in 277 parts by weight of methanol and agitated at room temperature for 1 hour. The white solid in the methanol was filtered by vacuum filtration.

The filtered white solid was suspended again in 277 parts by weight of methanol and agitated at room temperature for 1 hour. The white solid in the methanol was filtered by vacuum filtration. By drying the white solid, which was washed with methanol as described above, under reduced pressure at 60° C. until the weight became a constant weight, 42 parts by weight of cellulose acetate with a low degree of substitution was obtained. The measurement result of each physical property of the obtained cellulose acetate with a low degree of substitution is shown in Table 1.

Example A-2

Deacetylating and Precipitating:

By the same method as in Example A-1, 42 parts by weight of cellulose acetate with a low degree of substitution was obtained.

Purification:

Furthermore, this cellulose acetate with a low degree of substitution was added to 1440 parts by weight of water, agitated at room temperature for 8 hours, and allowed to stand still overnight. This suspension was subjected to centrifugal separation at 12600 G for 30 minutes, and a supernatant of the suspension was obtained. The supernatant was added dropwise in 10000 parts by weight of acetone under agitation, and white precipitates were obtained. By filtering the white precipitates by vacuum filtration and drying the white precipitates under reduced pressure at 60° C. until the weight became a constant weight, 54 parts by weight of cellulose acetate with a low degree of substitution was obtained. The measurement result of each physical property of the obtained cellulose acetate with a low degree of substitution is shown in Table 1.

Example A-3

Deacetylating and Precipitating:

By the method same as in Example A-1 except for using cellulose acetate available from Eastman Chemical Company (trade name "CA-320S", water content percentage: 3 wt. %; total degree of acetyl substitution: 1.80; degree of acetyl substitution at 2-position: 0.61; degree of acetyl substitution at 3-position: 0.56; degree of acetyl substitution at 6-position: 0.63) in place of the cellulose diacetate (trade name "L-50", available from Daicel Corporation; water content percentage: 3 wt. %) and changing the time for which the temperature was adjusted at 90° C. for 80 minutes, 47 parts by weight of cellulose acetate with a low degree of substitution was obtained. The measurement result of each physical property of the obtained cellulose acetate with a low degree of substitution is shown in Table 1.

Example A-4

By the method same as in Example A-1 except for using cellulose diacetate (trade name "LM-80", available from Daicel Corporation; water content percentage: 3 wt. %; total degree of acetyl substitution: 2.14: degree of acetyl substitution at 2-position: 0.75; degree of acetyl substitution at 3-position: 0.75; degree of acetyl substitution at 6-position: 0.64) in place of the cellulose diacetate (trade name "L-50", available from Daicel Corporation; water content percentage: 3 wt. %) and changing the time for which the temperature was adjusted (maintained) at 90° C. for 125 minutes, 41 parts by weight of cellulose acetate with a low degree of substitution was obtained. The measurement result of each physical property of the obtained cellulose acetate with a low degree of substitution is shown in Table 1.

Example A-5

By the method same as in Example A-1 except for using the cellulose diacetate (trade name "L-50", available from Daicel Corporation; water content percentage: 3 wt. %) and changing the time for which the temperature was adjusted (maintained) at 90° C. for 65 minutes, 45 parts by weight of cellulose acetate with a low degree of substitution was obtained. The measurement result of each physical property of the obtained cellulose acetate with a low degree of substitution is shown in Table 1.

Example A-6

By the method same as in Example A-1 except for using the cellulose diacetate (trade name "L-50", available from Daicel Corporation; water content percentage: 3 wt. %) and changing the time for which the temperature was adjusted (maintained) at 90° C. for 130 minutes, 38 parts by weight of cellulose acetate with a low degree of substitution was obtained. The measurement result of each physical property of the obtained cellulose acetate with a low degree of substitution is shown in Table 1.

Comparative Example A-1

Deacetylating:
In a mixture of 358 parts by weight of acetic acid and 95 parts by weight of water (mixed solvent) as a solvent, 100 parts by weight of cellulose diacetate (trade name "L-50", available from Daicel Corporation; water content percentage: 3 wt. %; total degree of acetyl substitution: 2.43; degree of acetyl substitution at 2-position: 0.86; degree of acetyl substitution at 3-position: 0.82; degree of acetyl substitution at 6-position: 0.75) as a raw material cellulose acetate was added, agitated at 70° C. for 5 hours, and allowed to stand still at room temperature (approximately 25° C.). This mixture was set to 70° C., 178 parts by weight of water was added, and thus a cellulose diacetate solution was obtained. The temperature of this cellulose diacetate solution was adjusted to 50° C., a mixture of 12.6 parts by weight of 98% sulfuric acid (catalyst) and 57 parts by weight of acetic acid (solvent) was added. The temperature was adjusted to 50° C. while this reaction mixture was agitated, after 4 hours from the sulfuric acid addition, 137 parts by weight of water was added over 30 minutes, and after 8 hours from the sulfuric acid addition, 111 parts by weight of water was added over 30 minutes. The temperature was adjusted to 50° C. while this reaction mixture was continuously agitated, after 23 hours 40 minutes (after 1420 minutes) from the sulfuric acid addition, a mixture of 72 parts by weight of sodium acetate trihydrate and 109 g of water was added, and the reaction was terminated.

Precipitating:
This reaction mixture was added dropwise to 4700 parts by weight of methanol under agitation, and white precipitates were obtained. Operation, in which the white precipitates were filtered and dispersed in 1100 parts by weight of methanol and filtered again, was repeated for 5 times. By drying the filtered white precipitates under reduced pressure at 60° C. until the weight became a constant weight, 62 parts by weight of cellulose acetate with a low degree of substitution was obtained. The measurement result of each physical property of the obtained cellulose acetate with a low degree of substitution is shown in Table 1.

Comparative Example A-2

Cellulose acetate with a low degree of substitution was obtained by the method in accordance with Example 17 of JP 6378712 B. The specific measurement procedure is as follows.

Deacetylating:
In a mixture of 510 parts by weight of acetic acid and 95 parts by weight of water, 100 parts by weight of cellulose diacetate (trade name "L-50", available from Daicel Corporation; water content percentage: 3 wt. %; total degree of acetyl substitution: 2.43; degree of acetyl substitution at 2-position: 0.86; degree of acetyl substitution at 3-position: 0.82; degree of acetyl substitution at 6-position: 0.75) was added, agitated at 70° C. for 3 hours, and a cellulose diacetate solution was obtained. The temperature of this cellulose diacetate solution was adjusted to 70° C. under agitation, 13 parts by weight of 98% sulfuric acid was added. The temperature was adjusted to 70° C. while this reaction mixture was continuously agitated, after 3 hours from the sulfuric acid addition, 67 parts by weight of water was added over 5 minutes, and after 8 hours from the sulfuric acid addition, 133 parts by weight of water was added over 10 minutes. The temperature was adjusted to 70° C. while this reaction mixture was continuously agitated, after 10 hours (after 600 minutes) from the sulfuric acid addition, the reaction mixture was cooled to 25° C., and the reaction was substantially terminated.

Precipitating:
The reaction mixture was added dropwise in 1500 parts by weight of acetone under agitation, and white precipitates were obtained. Operation, in which the white precipitates were filtered and dispersed in 800 parts by weight of acetone and filtered again, was repeated for 3 times. Operation, in which the filtered white precipitates were dispersed in 800 parts by weight of methanol containing 0.004 wt. % of potassium acetate and filtered again, was repeated for 2 times. The filtered white precipitates were dried under reduced pressure at 60° C. until the weight became a constant weight. For 64 parts by weight of this dried product, 960 parts by weight of 20 wt. % aqueous solution of acetone was added. After agitation was performed for 8 hours at 40° C., a thick phase was removed by centrifugal separation, parts by weight of acetone was added to a lean phase, and white precipitates were obtained. The white precipitates were filtered and dispersed in 3000 parts by weight of acetone and filtered again. By drying the filtered white precipitates under reduced pressure at 60° C. until the weight became a constant weight, 57 parts by weight of cellulose acetate with a low degree of substitution was obtained. The measurement result of each physical property of the obtained cellulose acetate with a low degree of substitution is shown in Table 1.

Comparative Example A-3

Cellulose acetate with a low degree of substitution was obtained according to conditions of Experiment No. 6 of Edgar et al., Macromolecules, 24, 3060 (1991).

Specifically, 60 parts by weight of cellulose diacetate (trade name "L-50", available from Daicel Corporation; dried under reduced pressure at 60° C. until the weight became a constant weight and used) was suspended in 237 parts by weight of methanol, 0.2 parts by weight of hexacarbonylmolybdenum $(Mo(CO)_6)$ was added, the internal pressure was adjusted to 200 psi by using nitrogen in a sealed reactor, and the temperature was adjusted at 140° C. for 7 hours (420 minutes). The reaction mixture was cooled to room temperature, and solids in the reaction mixture were filtered by vacuum filtration. By drying the filtered solids under reduced pressure at 60° C. until the weight became a constant weight, 34 parts by weight of cellulose acetate with a low degree of substitution was obtained. The measurement result of each physical property of the obtained cellulose acetate with a low degree of substitution is shown in Table 1.

Comparative Example A-4

Cellulose acetate with a low degree of substitution was obtained according to conditions of Experiment No. 7 of Edgar et al., Macromolecules, 24, 3060 (1991).

Specifically, 60 parts by weight of cellulose diacetate (trade name "L-50", available from Daicel Corporation; dried under reduced pressure at 60° C. until the weight became a constant weight and used) was suspended in 237 parts by weight of methanol, 0.2 parts by weight of molybdenum(VI) oxide $(MoO_3)$ was added, the internal pressure was adjusted to 1000 psi by using nitrogen in a sealed reactor, and the temperature was adjusted at 155° C. for 3 hours (180 minutes). The reaction mixture was cooled to room temperature, and solids in the reaction mixture were filtered by vacuum filtration. By drying the filtered solids under reduced pressure at 60° C. until the weight became a constant weight, 33 parts by weight of cellulose acetate with a low degree of substitution was obtained. The measurement result of each physical property of the obtained cellulose acetate with a low degree of substitution is shown in Table 1.

Comparative Example A-5

By the method same as in Example A-1 except for using the cellulose diacetate (trade name "L-50", available from Daicel Corporation; water content percentage: 3 wt. %) and changing the time for which the temperature was adjusted (maintained) at 90° C. for 50 minutes, 43 parts by weight of cellulose acetate with a low degree of substitution was obtained. The measurement result of each physical property of the obtained cellulose acetate with a low degree of substitution is shown in Table 1.

Comparative Example A-6

By the method same as in Example A-1 except for using the cellulose diacetate (trade name "L-50", available from Daicel Corporation; water content percentage: 3 wt. %) and changing the time for which the temperature was adjusted (maintained) at 90° C. for 160 minutes, 34 parts by weight of cellulose acetate with a low degree of substitution was obtained. The measurement result of each physical property of the obtained cellulose acetate with a low degree of substitution is shown in Table 1.

TABLE 1

| Experiment No. | Starting material | | | Hydrolysis reaction conditions | | | | Reaction product yield [wt. %] | Purification condition (centrifugal separation conditions) | | | | Purified product yield [wt. %] | Analysis results | | | | | | |
|---|---|---|---|---|---|---|---|---|---|---|---|---|---|---|---|---|---|---|---|---|
| | Name | Total degree of acetyl substitution (DS) (—) | Degree of acetyl substitution at 6-position (DS$_6$) (—) | Solvent | Catalyst | TEMPERATURE (°C) | TIME [min] | | Cellulose acetate [part by weight] | Water [part by weight] | Centrifugal force [G] | TIME [min] | | Total degree of acetyl substitution (DS) (—) | Degree of acetyl substitution at 2-position (DS$_2$) (—) | Degree of acetyl substitution at 3-position (DS$_3$) (—) | Degree of acetyl substitution at 6-position (DS$_6$) (—) | Proportion of degree of acetyl substitution at 6-position (%) | Degree of polymerization (—) | Transmittance (%) |
| Example A-1 | L-50 | 2.43 | 0.75 | Methanol | Sulfuric acid | 90 | 100 | 87 | — | — | — | — | — | 0.58 | 0.77 | 0.25 | 0.06 | 10.3 | 26 | 12 |
| Example A-2 | L-50 | 2.43 | 0.75 | Methanol | Sulfuric acid | 90 | 100 | 87 | 42 | 1440 | 12600 | 30 | 90 | 0.55 | 0.26 | 0.24 | 0.05 | 9.1 | 24 | 93 |
| Example A-3 | CA-320S | 1.80 | 0.63 | Methanol | Sulfuric acid | 90 | 80 | 90 | — | — | — | — | — | 0.53 | 0.26 | 0.22 | 0.05 | 9.4 | 28 | 92 |
| Example A-4 | LM-80 | 2.14 | 0.64 | Methanol | Sulfuric acid | 90 | 125 | 85 | — | — | — | — | — | 0.40 | 0.18 | 0.15 | 0.07 | 17.0 | 29 | 12 |
| Example A-5 | L-50 | 2.43 | 0.75 | Methanol | Sulfuric acid | 90 | 65 | 88 | — | — | — | — | — | 0.85 | 0.41 | 0.35 | 0.10 | 12.0 | 65 | 6 |
| Example A-6 | L-50 | 2.43 | 0.75 | Methanol | Sulfuric acid | 90 | 130 | 83 | — | — | — | — | — | 0.41 | 0.19 | 0.18 | 0.04 | 9.8 | 11 | 14 |
| Comparative Example A-1 | L-50 | 2.43 | 0.75 | Aqueous solution of acetic acid | Sulfuric acid | 50 | 1420 | 89 | — | — | — | — | — | 0.65 | 0.22 | 0.19 | 0.24 | 36.9 | 306 | 80 |
| Comparative Example A-2 | L-50 | 2.43 | 0.75 | Acetic acid aqueous solution | Sulfuric acid | 70 | 600 | 80 | — | — | — | — | — | 0.78 | 0.27 | 0.23 | 0.28 | 35.9 | 117 | 85 |
| Comparative Example A-3 | L-50 | 2.43 | 0.75 | Methanol | Mo(CO)$_6$ | 140 | 420 | 82 | — | — | — | — | — | 0.48 | 0.24 | 0.19 | 0.05 | 10.4 | 218 | 2 |
| Comparative Example A-4 | L-50 | 2.43 | 0.75 | Methanol | MoO$_3$ | 155 | 180 | 80 | — | — | — | — | — | 0.50 | 0.25 | 0.19 | 0.06 | 12.0 | 58 | 2 |
| Comparative Example A-5 | L-50 | 2.43 | 0.75 | Methanol | Sulfuric acid | 90 | 50 | 82 | — | — | — | — | — | 1.00 | 0.47 | 0.40 | 0.13 | 13.1 | 86 | 2 |

TABLE 1-continued

| Experiment No. | Starting material | | | Hydrolysis reaction conditions | | | | Reaction product yield [wt. %] | Purification condition (centrifugal separation conditions) | | | | Purified product yield [wt. %] | Analysis results | | | | | | |
|---|---|---|---|---|---|---|---|---|---|---|---|---|---|---|---|---|---|---|---|---|
| | Name | Total degree of acetyl substitution (DS) (—) | Degree of acetyl substitution at 6-position (DS$_6$) (—) | Solvent | Catalyst | TEMPERATURE (° C.) | TIME [min] | | Cellulose acetate [part by weight] | Water [part by weight] | Centrifugal force [G] | TIME [min] | | Total degree of acetyl substitution (DS) (—) | Degree of acetyl substitution at 2-position (DS$_2$) (—) | Degree of acetyl substitution at 3-position (DS$_3$) (—) | Degree of acetyl substitution at 6-position (DS$_6$) (—) | Proportion of degree of acetyl substitution at 6-position (%) | Degree of polymerization (—) | Transmittance (%) |
| Comparative Example A-6 | L-50 | 2.43 | 0.75 | Methanol | Sulfuric acid | 90 | 160 | 75 | — | — | — | — | — | 0.33 | 0.17 | 0.13 | 0.03 | 9.1 | 10 | 1 |

For the cellulose acetate of Comparative Example A-1, the degree of acetyl substitution at 6-position was 0.24, and the proportion of the degree of acetyl substitution at 6-position in the total degree of acetyl substitution was 36.9%. For the cellulose acetate of Comparative Example A-2, the degree of acetyl substitution at 6-position was 0.28, and the proportion of the degree of acetyl substitution at 6-position in the total degree of acetyl substitution was 35.9%. Thus, for the cellulose acetates of Comparative Examples A-1 and A-2, the degree of acetyl substitution at 6-position was higher than each of the degrees of acetyl substitution at 2-position and 3-position.

For the cellulose acetate of Comparative Example A-3, the degree of acetyl substitution at 6-position was 0.05, and the proportion of the degree of acetyl substitution at 6-position in the total degree of acetyl substitution was 10.4%. For the cellulose acetate of Comparative Example A-4, the degree of acetyl substitution at 6-position was 0.06, and the proportion of the degree of acetyl substitution at 6-position in the total degree of acetyl substitution was 12.0%. Thus, for the cellulose acetates of Comparative Examples A-3 and A-4, the degree of acetyl substitution at 6-position was lower than each of the degrees of acetyl substitution at 2-position and 3-position. However, the light transmittance at 660 nm of 4 wt. % aqueous solution was low, and the water solubility was poor.

For the cellulose acetate of Comparative Example A-5, the degree of acetyl substitution at 6-position was 0.13, and the proportion of the degree of acetyl substitution at 6-position in the total degree of acetyl substitution was 13.1%. For the cellulose acetate of Comparative Example A-6, the degree of acetyl substitution at 6-position was 0.03, and the proportion of the degree of acetyl substitution at 6-position in the total degree of acetyl substitution was 9.1%. Thus, for the cellulose acetates of Comparative Examples A-5 and A-6, the degree of acetyl substitution at 6-position was lower than each of the degrees of acetyl substitution at 2-position and 3-position. However, the light transmittance at 660 nm of 4 wt. % aqueous solution was low, and the water solubility was poor.

Meanwhile, the cellulose acetates of Examples A-1 to A-6 each had a low proportion, which was 18% or less, of the degree of acetyl substitution at 6-position in the total degree of acetyl substitution and a light transmittance at 660 nm of 4 wt. % aqueous solution was 5% or greater, and exhibited excellent water solubility. Especially, the light transmittance at 660 nm of 4 wt. % aqueous solution of each of Marked-up Specification the cellulose acetates of Examples A-2 and A-3 was 92% or greater, and the water solubility was especially excellent.

Animal Experiment (Acetyl Group Remaining Ratio, Feed Intake, Body Weight Gain, Blood Sugar Level, Cholesterol, Neutral Fat, Epididymal Fat)

Animal experiment was initiated by using 9 male Wistar rats (Japan SLC, Inc.) that were 7 weeks old (body weight: 150 to 170 g) and that were separately fed in stainless steel cages under conditions at room temperature of 24±1° C., relative humidity of 55±5° C., and a light and dark cycle of 12 hours (light from 7:00 to 19:00).

After the rats were brought in, the rats were acclimatized for 3 days by feeding Purified diet AIN-93G (Reeves et al., Journal of Nutrition, 123, 1939-1951 (1993)) and tap water. Then, the rats were separated into three groups based on body weight (in a manner that the total body weight of rats in the groups were not biased). In addition to tap water, the first group was free-fed with AIN-93G (may be also referred to as "control group"), the second group was free-fed with AIN-93G containing 5 wt. % of cellulose acetate with a low degree of substitution of Example A-2 (may be also referred to as "test group"), and the third group was free-fed with AIN-93G containing 5 wt. % of cellulose acetate with a low degree of substitution of Comparative Example A-1 (may be also referred to as "comparison group") for 14 days. The number of rats per group was 3, for all groups. The first group corresponded to Reference Example B-1, the second group corresponded to Example B-1, and the third group corresponded to Comparative Example B-1.

On the third day, seventh day, and thirteenth day of initiation of the feeding by separating the rats into the three groups and by corresponding feed, fecal matters of the entire day were collected and used for analysis of acetyl group remaining ratio. The analysis method is as described below. Furthermore, during the feeding period, feed intake and body weight gain were measured.

On the fourteenth day of the feeding, the rats were fasted from 7 o'clock in the morning, and autopsies were performed from 15 o'clock. The abdomen of the rat was opened up with isoflurane anesthesia, and approximately 2 mL of blood was taken from abdominal aorta into a heparin tube (VENOJECT II Sodium Heparin, for 3 mL blood sampling; Terumo Corporation). Then, the rat was euthanized by exsanguination, and epididymal fat (left and right) was rapidly extracted. The epididymal fat weight was then measured.

The sampled blood was subjected to centrifugal separation at 2380 G at room temperature for 10 minutes, and blood plasma was isolated. On the day of the blood sampling, for the isolated plasma, the blood sugar level was measured by using CicaLiquid GLU (Kanto Chemical Co., Inc.); the neutral fat (triglycerides) was measured by using CicaLiquid-N TG (Kanto Chemical Co., Inc.); and the cholesterol (also referred to as plasma cholesterol) was measured by using CicaLiquid-N CHO (Kanto Chemical Co., Inc.).

Acetyl Group Remaining Ratio

The acetic acid concentration of the rat fecal matters was determined by suspending 0.1 g of the rat fecal matters in 10 mL of water, and derivatizing the acetic acid contained in the rat fecal matters into corresponding 2-nitrophenylhydrazide and quantitating the 2-nitrophenylhydrazide of the acetic acid by HPLC analysis in accordance with the method by Miwa et al. (Journal of Chromatography, 321, 165-174 (1985)).

Furthermore, the acetic acid concentration of sodium hydroxide-treated rat fecal matters was determined by suspending 0.1 g of the rat fecal matters in 150 mM sodium hydroxide aqueous solution and the temperature thereof was adjusted at 70° C. for 4 hours, and derivatizing the acetic acid contained in the sodium hydroxide-treated rat fecal matters into corresponding 2-nitrophenylhydrazide and quantitating the 2-nitrophenylhydrazide of the acetic acid by HPLC analysis in accordance with the method by Miwa et al. (Journal of Chromatography, 321, 165-174 (1985)).

The difference between the acetic acid concentration of the sodium hydroxide-treated rat fecal matters and the acetic acid concentration of the rat fecal matters suspended in water was used as the acetyl group concentration of the rat fecal matters (mole per unit weight). The acetyl group remaining ratio was determined by the following equation.

$$\text{Acetyl group remaining ratio(mol \%)} = 100 \times (\text{acetyl group concentration of rat fecal matters}) \times A/(B \times C/D)$$

A: Rat fecal matter amount (weight) of 0 to 24 hours
B: Feed intake (weight) of rat of −24 hours to 0 hours
C: Concentration (wt. %) of cellulose acetate in feed
D: Number of moles of acetyl groups per unit weight of the cellulose acetate=DS/(162.14+42.037× DS)
DS: Total degree of acetyl substitution

TABLE 2

|  |  |  | Reference Example B-1 (control group) | Example B-1 (test group: cellulose acetate of Example A-2) | Comparative Example B-1 (comparison group: cellulose acetate of Comparative Example A-1) |
|---|---|---|---|---|---|
| Acetyl group remaining ratio | Day 3 of feeding | [mol %] | 0 | 21 | 36 |
|  | Day 7 of feeding | [mol %] | 0 | 26 | 37 |
|  | Day 13 of feeding | [mol %] | 0 | 16 | 23 |
| Feed intake |  | [g] | 227 | 198** | 207* |
| Body weight gain |  | [g] | 53.9 | 37.9* | 49.4 |
| Blood sugar level |  | [mg/dL] | 257 | 210 | 186* |
| Cholesterol |  | [mg/dL] | 72 | 53 | 58 |
| Neutral fat (triglycerides) |  | [mg/dL] | 91 | 69* | 71 |
| Epididymal fat weight |  | [g] | 4.1 | 3.1** | 3.1** |

*Significant when $p < 0.05$ relative to control group (Dunnett's test)
**Significant when $p < 0.01$ relative to control group (same)

The acetyl group remaining ratios of the fecal matters in the case (Example B-1) where the cellulose acetate of Example A-2 (the proportion of the degree of acetyl substitution at 6-position in the total degree of acetyl substitution was 18% or less) was fed to the rats on the third day, seventh day, and thirteenth day of the feeding was lower than those of the case (Comparative Example B-1) where the cellulose acetate of Comparative Example A-1 (the proportion of the degree of acetyl substitution at 6-position in the total degree of acetyl substitution was greater than 18%) was fed to the rats. This indicates that the cellulose acetate of Example having a low proportion of the degree of acetyl substitution at 6-position exhibited excellent degradability and was ready to be metabolized in the body.

The feed intake of the rats in Comparative Example B-1 (comparison group) was significantly lower than that of Reference Example B-1 (control group); however, there was no significant difference in body weight increases. On the other hand, the feed intake and the body weight gain of the rats in Example B-1 (test group) were lower than those of Comparative Example B-1 (comparison group), and clearly exhibited significant differences with respect to Reference Example B-1 (control group).

The blood sugar level and the cholesterol of the rats in Example B-1 (test group) exhibited tendency of decrease with respect to those of Reference Example B-1 (control group) although the difference was not significant.

Furthermore, there was no significant difference between the neutral fat of the rats in Comparative Example B-1 (comparison group) and that of Reference Example B-1 (control group). On the other hand, the neutral fat of the rats in Example B-1 (test group) was lower than that of Reference Example B-1 (control group), and there was a significant difference.

Furthermore, the epididymal fats of the rats in Comparative Example B-1 (comparison group) and Example B-1 (test group) were less than that of Reference Example B-1 (control group), and there was a significant difference.

As described above, it was found that the cellulose acetate of Example having a low proportion of degree of acetyl substitution at 6-position exhibits excellent degradability, is readily metabolized in the body, and particularly contributes to appetite suppression (feed intake suppression), body weight increase suppression, neutral fat suppression, and fat accumulation suppression (epididymal fat suppression) of rats.

The invention claimed is:
1. A cellulose acetate having:
a total degree of acetyl substitution of 0.4 or greater and 0.9 or less,
a proportion of a degree of acetyl substitution at 6-position in the total degree of acetyl substitution of 18% or less and greater than 0%,
a viscosity-average degree of polymerization of 3 or greater and 65 or less, and
a light transmittance at 660 nm of 5% or greater in 4 wt. % aqueous solution.
2. The cellulose acetate according to claim 1, having the light transmittance at 660 nm of 80% or greater in 4 wt. % aqueous solution.
3. The A cellulose acetate according to claim 1, wherein the proportion of a degree of acetyl substitution at 6-position in the total degree of acetyl substitution is 18% or less and 0.63% or greater.
4. A method for producing the cellulose acetate according to claim 1, the method comprising:
deacetylating by subjecting a raw material cellulose acetate having a total degree of acetyl substitution from 1.5 to 3.0 to solvolysis, and
precipitating a cellulose acetate that is formed by the deacetylating of the raw material cellulose acetate, wherein
the solvolysis of the raw material cellulose acetate is allowed to progress in the presence of a solvent containing an alcohol having 3 carbons or less, and an acid catalyst at a temperature that is not lower than a boiling point of the alcohol,
the acid catalyst is sulfuric acid,
the solvent optionally contains a component other than the alcohol having 3 carbons or less, which is present at an amount of 30 wt. % or less, and
a time of the solvolysis reaction is 60 minutes or longer and 150 minutes or less.

5. The method for producing the cellulose acetate according to claim 4, wherein the acid catalyst has an acid dissociation constant pKa in water at 25° C. of 0 or less.

6. The method for producing the cellulose acetate according to claim 4, wherein the alcohol is methanol.

7. The method for producing the cellulose acetate according to claim 4, wherein the solvent contains acetate.

8. The method for producing the cellulose acetate according to claim 4, the method further comprising:

removing a residue by dissolving the precipitated cellulose acetate in water, and depositing the dissolved cellulose acetate.

9. The method for producing the cellulose acetate according to claim 4, the method further comprising:

removing a residue by dissolving the precipitated cellulose acetate in water and performing centrifugal separation, and reprecipitating the dissolved cellulose acetate.

10. A method for appetite suppression, which comprises administering to a patient in need thereof the cellulose acetate according to claim 1.

11. A method for appetite suppression, which comprises administering to a patient in need thereof the cellulose acetate according to claim 2.

12. A method for body weight increase suppression, which comprises administering to a patient in need thereof the cellulose acetate according to claim 1.

13. A method for body weight increase suppression, which comprises administering to a patient in need thereof the cellulose acetate according to claim 2.

14. A method for neutral fat suppression, which comprises administering to a patient in need thereof the cellulose acetate according to claim 1.

15. A method for neutral fat suppression, which comprises administering to a patient in need thereof the cellulose acetate according to claim 2.

16. A method for fat accumulation suppression, which comprises administering to a patient in need thereof the cellulose acetate according to claim 1.

17. A method for fat accumulation suppression, which comprises administering to a patient in need thereof the cellulose acetate according to claim 2.

* * * * *